United States Patent [19]

Mochida et al.

[11] 4,218,335
[45] Aug. 19, 1980

[54] STABILIZER FOR AN IMMUNOCHEMICAL MEASURING REAGENT

[75] Inventors: Ei Mochida, Tokyo; Nobuhisa Ogawa, Omiya, both of Japan

[73] Assignee: Mochida Seiyaku Kabushiki Kaisha, Tokyo, Japan

[21] Appl. No.: 960,639

[22] Filed: Nov. 14, 1978

[30] Foreign Application Priority Data

Nov. 29, 1977 [JP] Japan .................. 52/142925

[51] Int. Cl.² ...................... G01N 33/16; G01N 31/02
[52] U.S. Cl. .................................. 252/408; 23/230 B; 23/915; 260/115; 424/12; 435/7; 435/188
[58] Field of Search .............. 23/230 B, 915; 260/115; 424/12; 252/408; 435/7, 188

[56] References Cited

U.S. PATENT DOCUMENTS

| | | | |
|---|---|---|---|
| 3,215,685 | 11/1965 | Nakanishi | 260/115 X |
| 3,371,081 | 2/1968 | Nakanishi | 260/115 |
| 3,391,131 | 7/1968 | Zahn | 260/115 |
| 3,642,978 | 2/1972 | Ogawa | 260/115 X |
| 4,003,988 | 1/1977 | Hoff | 424/12 |

FOREIGN PATENT DOCUMENTS 1143938  2/1969  United Kingdom .

OTHER PUBLICATIONS

"Methods in Enzymology", S. P. Colowick et al., eds., vol. II, 754–755, Academic Press, New York, 1955.

Primary Examiner—Sidney Marantz
Attorney, Agent, or Firm—Brisebois & Kruger

[57] ABSTRACT

A stabilizer consisting principally of cytochrome c or a thermally modified matter of cytochrome c for maintaining constant over an extended period the sensitivity of measurement and specificity of a measuring reagent on the basis of the immunochemical agglutination reaction and the agglutination inhibition reaction.

15 Claims, 2 Drawing Figures

STABILIZER FOR AN IMMUNOCHEMICAL MEASURING REAGENT

BACKGROUND OF THE INVENTION

A number of immunochemical methods have so far been used for measurement of physiologically active substances contained in body fluids such blood, urine and the like. Among them, a measuring reagent using finely divided granular solids such as blood cells, high molecular latexes, etc. as a carrier for the antigen or antibody on the basis of the immunochemical agglutination reaction or agglutination inhibition reaction has found wide applications in the measurement of the abovementioned physiologically active substances because it can be easily employed and rapidly provides the results of measurement.

The reagent is used, for example, for the diagonis of pregnancy by way of measurement of gonadotropin (hCG) contained in the serum or urine of a woman who might be pregnant, or for the diagnosis of growth of an fetus by measuring esteriol in the urine of a pregnant woman.

Accordingly, the essential requirements for the reagent are as follows. First, the reagent must have such a high sensitivity of measurement that when even a trace amount of a matter to be detected is present, the reagent causes the agglutination reaction or the agglutination inhibition reaction on the basis of the immunochemical reaction occurring between the matter to be detected and the reagent, and thus enables the measurement of the matter to be detected. Second, the reagent must have such a high specificity that unless the matter to be detected is present, the reagent does not cause the agglutination reaction or the agglutination inhibition reaction. Furthermore, the reagent must maintain the sensitivity and the specificity as they are immediately after the production of the reagent even after the reagent is stored for an extended period of time. That is to say, the reagent must have good storability.

It has heretofore been difficult for a reagent using finely divided solid particles to keep its sensitivity of measurement and specificity as they are immediately after the production for a long period of time. Hence, the reagent has the disadvantages that it has a short effective period or frequently provides a measurement error even during the effective period.

To cope with these problems, there have conventionally been proposed various methods including, for example, a method of covering in advance the finely divided solid particles with a protein that does not participate in the immunoreaction and then letting the antigen or the antibody to be absorbed onto the finely divided solid particles, or a method of first letting the antigen or the antibody to be adsorbed onto the finely divided solid particles and then treating them with a protein solution that does not participate in the immuno-reaction (Japanese Patent Publication No. 12,471/1968, Japanese Patent Publication No. 11,407/1974, Japanese Patent Laid-Open Publication No. 82,230/1975).

These prior art methods use, as the proteins that do not participate in the immuno-reaction, blood serum albumin (BSA), egg albumin (EA), lactoalbumin, hemoglobin, blood serum globulin, lactoglobulin, and the like. Though these proteins provide certain effects, their effects are not entirely satisfactory.

The inventors of the present invention has made intensive studies in search for a stabilizer which enables a reagent to sufficiently maintain its high measuring sensitivity and specificity over an extended period of time, and now found that cytocrome c provides outstanding effect. The present invention is completed on the basis of this finding.

SUMMARY OF THE INVENTION

It is an object of the present invention to provide a stabilizer for maintaining over an extended period of time the sensitivity of measurement and specificity of a measuring reagent based on the immunochemical agglutination reaction or agglutination inhibition reaction.

It is another object of the present invention to provide a process for producing the abovementioned stabilizer.

It is still another object of the present invention to provide a measuring reagent capable of maintaining its measuring sentitivity and specificity over an extended period of time.

DETAILED DESCRIPTION OF THE INVENTION

The present invention relates to a stabilizer for an immunochemical measuring reagent, a process for producing said stabilizer and a process for using the same.

The stabilizer of the present invention is obtained by dissolving cytochrome c in a concentration of from 0.01 to 5%, preferably from 0.1 to 1.0%, in a 0.05–0.2% sodium azide solution and then dialyzing the solution for a night in a buffer solution such as, for example, a glycine saline buffer (hereinafter referred to as GBS: pH 8.2).

The concentration of cytochrome c must not be lower than 0.01%, or else desired effects could not be obtained. Though there is no critical upper limit to the concentration of cytochrome c, it is practically desirable that the concentration is not higher than 5%, especially not higher than 1%.

The stabilizer in accordance with the present invention provides further advantageous effect when it is subjected to the heat-treatment. Namely, after 0.01–5%, preferably 0.1–1.0%, in concentration of cytochrome c is dissolved in a 0.05–0.2% sodium azide solution, the solution is heated by an autoclave to 100–130° C. for 2–8 hours. After solidified matters formed by the heating are removed, the resulting solution is dialyzed in a buffer solution such as GBS, for example, to thereby give the stabilizer of the invention.

It is preferred that the heating temperature is in the range of from 100° to 130° C., especially from 115° to 125° C., and the heating time is from 2 to 8 hours.

During the production of the stabilizer, instead of the dialysis of the cytochrome c solution with buffer solution, each of composition ingredients of the buffer solution is added so as to become each in a desired concentration and then adjusting the pH to a desired level.

Figure 1:
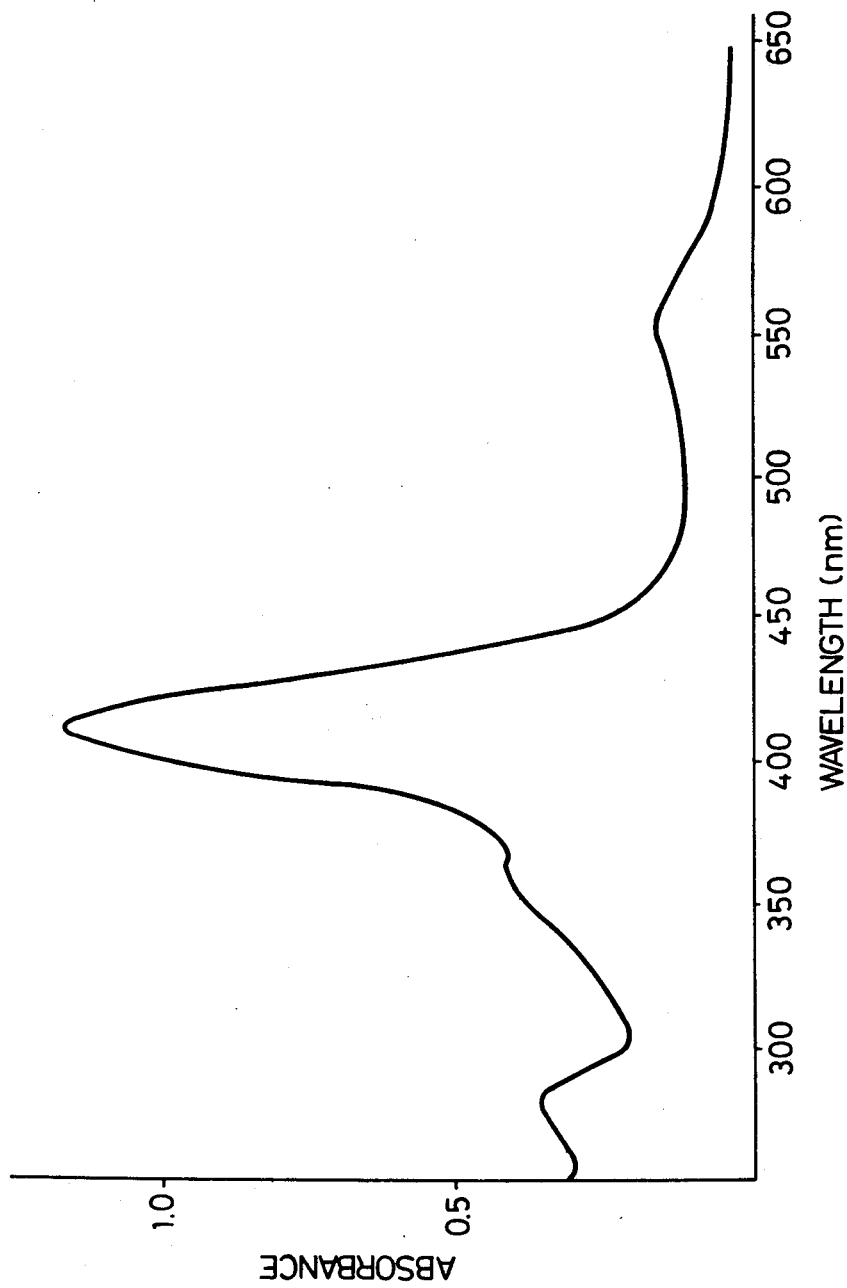
FIG. 1 is an absorption spectrum of a stabilizer consisting principally of native cytochrome c.
Figure 2:
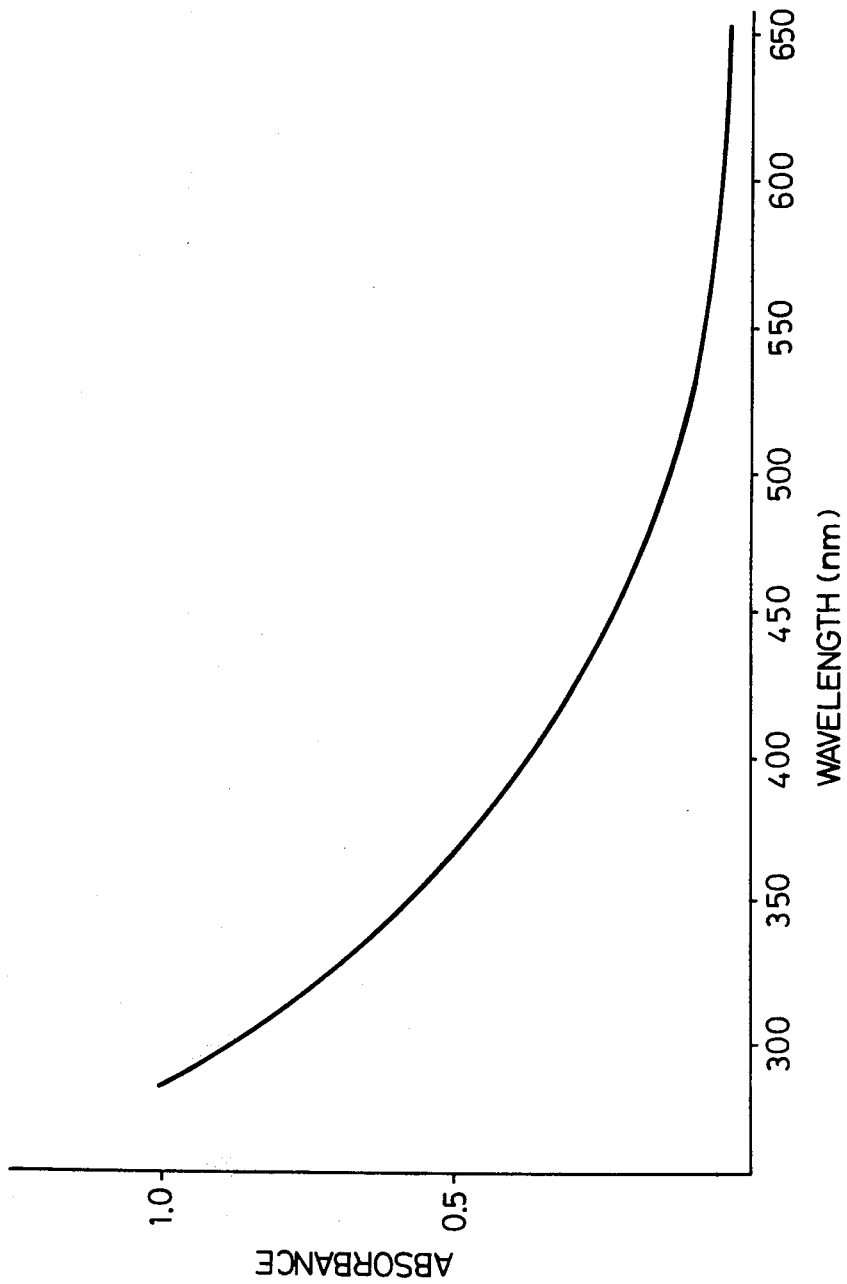
FIG. 2 is an absorption spectrum of a stabilizer consisting principally of thermally modified cytochrome c.

FIGS. 1 and 2 illustrate the absorption spectra of the stabilizer in accordance with the present invention.

FIG. 1 illustrates an absorption spectrum of the stabilizer consisting principally of native cytochrome c in the visible range. The peak of absorption specific to cytochrome c is observed at 550 nm.

FIG. 2 illustrates an absorption spectrum in visible range of the stabilizer consisting principally of a thermally modified matter of cytochrome c. It can be seen that due to the thermal modification, the absorption at 550 nm specific to cytochrome c disappears and the gradual increase of the absorption is shown towards the short wave length range.

In order to obtain a reagent capable of maintaining its measuring sensitivity and specificity for an extended period by the use of the stabilizer of the present invention, the finely divided solid particles having adsorbed thereon the antigen or the antibody are treated with the stabilizer of the present invention. In this instance, more improved effects can be obtained by allowing, at the same time, a buffer solution for diluting the specimen to contain the stabilizer of the present invention.

The treatment of the finely divided solid particles with the present stabilizer is effected in the following manner. A buffer solution dissolving therein the antigen or the antibody is admixed with a suspension of the finely divided solid particles so as to allow the particles to adsorb the antigen or the antibody, and then centrifugally separated. Next, the stabilizer of the invention is added to and mixed with the resulting precipitate. After the finely divided solid particles are centrifugally separated, the resulting precipitate is again suspended in the buffer solution.

The buffer solution for diluting the specimen is caused to contain the stabilizer of this invention in the following manner. Components of the buffer solution to be used, e.g., glycine and sodium chloride in the case of GBS, are added to a heat-treated solution of cytochrome c or thermally modified cytochrome c so that their concentration becomes to 0.75% and 0.85%, respectively. After sodium azide is added in a final concentration of 0.1%, a pH of the solution is adjusted to 8.2 using a 1/10. N sodium hydroxide solution.

In addition to the abovementioned GBS, buffer solutions used ordinarily in the field of the immunochemistry such as phosphate buffer saline solution (PBS), borate buffer saline solution (BBS), etc., may be used as the buffer solution.

The stabilizer in accordance with the present invention is effective for stabilizing a measuring reagent using the finely divided solid particles. Especially, the present stabilizer is effective for stabilizing such a reagent that uses, as the finely divided solid particles, blood cells of various animals, high molecular latexes (e.g. polystyrene latex, styrene-butadiene copolymer latex, styrene-divinylbenzene copolymer latex), or high molecular latexes having introduced therein a functional group such as a hydroxyl group or a carboxyl group.

In addition to the cytochrome c of the horse heart muscle, the cytochrome c of the bovine heart muscle and the yeast cytochrome c may be likewise used as the cytochrome c to be used in the present invention.

The present invention will be explained in further detail with reference to the following Experimental Examples and Examples.

EXPERIMENTAL EXAMPLE 1

This example illustrates the comparison of effects between the stabilizer in accordance with the present invention and proteins that have been conventionally employed.

The stabilizers of the present invention are prepared by treating cytochrome c in accordance with the method of the later-appearing Example 1 or 2. As the conventional proteins used, each of BSA and EA is dissolved in a concentration of 0.1% is GBS. The finely divided solid particles used are polystyrene latex particles that are allowed to adsorb the antibody in accordance with the method described in the later-appearing Example 6, and thereafter a reagent is prepared by treating the same with each of the abovementioned stabilizers or proteins.

A buffer solution for diluting the specimen containing the stabilizer of the present invention is prepared in accordance with the method of Example 3. The abovementioned reagents and the buffer solution are stored at 37° C. over periods illustrated in Table 1.

After the end of each predetermined period, the reagents treated with the stabilizer of the invention are combined with the abovementioned buffer solution for diluting the specimen while the reagents treated with BSA or EA are combined with a buffer solution for diluting the specimen which does not contain the stabilizer. Next, hCG is measured for each reagent in order to determine change in its measuring sensitivity and occurrence of a non-specific reaction. The sensitivity of measurement is expressed in terms of the strength of agglutination at the time of measurement of hCG of 1 iu/ml and 0.5 iu/ml, and the non-specific reaction is expressed in terms of the strength of agglutination at the time of measurement of a non-pregnant urine which does not contain hCG.

The strength of agglutination is evaluated in accordance with the following standard:

++: Exhibits a strong agglutination by visual observation.

+: Exhibit a clear agglutination by visual observation.

±: Exhibits an obscure agglutination by visual observation.

−: Exhibits no agglutination by visual observation.

Table 1

| | | Concentration of hCG (iu/ml) | Period of Storage | | | |
| --- | --- | --- | --- | --- | --- | --- |
| | | | Immediately after production | 1 month | 3 months | 6 months |
| Stabilizer of this invention | Stabilizer consisting principally of native cytochrome c | 1.0 | ++ | ++ | ++ | ++ |
| | | 0.5 | + | + | + | + |
| | | 0 | − | − | − | ± |
| | Stabilizer consisting principally of thermally modified cytochrome c | 1.0 | ++ | ++ | ++ | ++ |
| | | 0.5 | + | + | + | + |
| | | 0 | − | − | − | − |
| | | 1.0 | ++ | ++ | ++ | + |

Table 1-continued

|  |  | Concentration of hCG (iu/ml) | Period of Storage | | | |
|---|---|---|---|---|---|---|
|  |  |  | Immediately after production | 1 month | 3 months | 6 months |
| Conventional proteins | BSA | 0.5 | + | + | + | ± |
|  |  | 0 | − | − | ± | + |
|  |  | 1.0 | ++ | ++ | ++ | ++ |
|  | EA | 0.5 | + | + | + | ++ |
|  |  | 0 | − | − | + | ++ |

Among the stabilizers of the present invention, one consisting principally of native cytochrome c causes a slight change in its specificity after the end of 6 months' storage, but the stabilizer consisting principally of the thermally modified substances and the non-specific reaction even after storage for an extended period of time. In the case of BSA, though its measuring sensitivity can be retained relatively well, the non-specific reaction becomes progressively strong with the passage of the storing period, thereby losing the reliability of the reagent. In the case of the use of EA, the sensitivity of measurement increases with the passage of the storing period and exhibits a strong agglutination even for a non-pregnant urine which does not contain hCG whereby the measurement of hCG becomes meaningless.

Incidentally, deterioration of the reagents may be classified into the following four groups, and BSA belongs to Type II and EA does to Type III.

Table 2

|  | Type I | Type II | Type III | Type IV |
|---|---|---|---|---|
| Sensitivity of measurement | → | ↓ | ↑ | ↓ |
| Non-specific reaction | ↑ | ↑ | ↑ | → |

→ no change
↑ increase
↓ decrease

EXPERIMENTAL EXAMPLE 2

A reagent obtained by treating the finely divided solid particles with the stabilizer consisting of the thermally modified cytochrome c, a reagent without any stabilization treatment, a buffer solution for diluting the specimen containing the abovementioned stabilizer and a buffer solution for diluting the specimen not containing the stabilizer are stored at 37° C. for each period shown in Table 3 and after the passage of each period, combined in the combination also shown in Table 3 for measuring the hCG and determining the effects of the stabilizer.

As can be seen from Table 3, the maximum stabilization effect can be obtained by combining the reagent treated with the stabilizer and the buffer solution for diluting the specimen containing the stabilizer. However, the stabilization effect to a certain extent is also observed in the case where the reagent alone is treated with the stabilizer. The evaluation standard in this instance is the same as that of Experimental Example 1.

Table 3

| Combination of reagent and buffer solution for diluting specimen | Concentration of hCH (iu/ml) | Period of storage | | | |
|---|---|---|---|---|---|
|  |  | Immediately after production | 1 month | 3 months | 6 months |
| Stabilized reagent and buffer solution containing stabilizer | 1.0 | ++ | ++ | ++ | ++ |
|  | 0.5 | + | + | + | + |
|  | 0 | − | − | − | − |
| Stabilized reagent and buffer solution not containing stabilizer | 1.0 | ++ | ++ | ++ | ++ |
|  | 0.5 | + | + | + | ++ |
|  | 0 | − | − | ± | + |
| Unstabilized reagent and buffer solution containing stabilizer | 1.0 | ++ | ++ | ++ | ++ |
|  | 0.5 | + | + | ++ | ++ |
|  | 0 | − | − | + | ++ |
| Unstabilized reagent and unstabilized buffer solution | 1.0 | ++ | ++ | ++ | ++ |
|  | 0.5 | + | ++ | ++ | ++ |
|  | 0 | − | + | ++ | ++ |

EXPERIMENTAL EXAMPLE 3

This example investigates the effect of the stabilizers in accordance with the change in the concentration of cytochrome c. The experimental procedures and the evaluation standard are the same as those of Experimental Example 1. As illustrated in Table 4, lowering of the sensitivity of measurement and occurrence of the non-specific reaction are observed in the concentration of 0.01% after storage for an extended period of time, but the excellent effects are observed in the concentration exceeding 0.1%.

Table 4

| Concentration of cytochrome c (%) | Concentration of hCG (iu/ml) | Period of storage | | | |
|---|---|---|---|---|---|
|  |  | Immediately after production | 1 month | 3 months | 6 months |
| 0.01 | 1.0 | ++ | ++ | ++ | ++ |
|  | 0.5 | + | + | + | ± |
|  | 0 | − | − | ± | + |
| 0.1 | 1.0 | ++ | ++ | ++ | ++ |
|  | 0.5 | + | + | + | + |
|  | 0 | − | − | − | − |
| 1.0 | 1.0 | ++ | ++ | ++ | ++ |
|  | 0.5 | + | + | + | + |
|  | 0 | − | − | − | − |
| 5.0 | 1.0 | ++ | ++ | ++ | ++ |
|  | 0.5 | + | + | + | + |
|  | 0 | − | − | − | − |

EXAMPLE 1

Cytochrome c of the horse heart muscle is dissolved in a concentration of 0.3% in a 0.1% sodium azide solution, and the resulting solution is dialyzed in GBS (pH 8.2) for a night to thereby give the stabilizer.

EXAMPLE 2

Cytochrome c of the bovine heart muscle is dissolved in a concentration of 0.5% in a 0.1% sodium azide solution, and the resulting solution is heat-treated in an autoclave at 121° C. for 6 hours. After the solidified matters formed are removed by filtration, the filtrate is dialyzed in GBS for a night.

EXAMPLE 3

A yeast cytochrome c is dissolved in a 0.1% sodium azide solution, and the resulting solution is heat-treated in an autoclave at 121° C. for 4 hours. After the solidified matters formed are removed, glycine, sodium chloride and sodium azide are added to the filtrate so that their concentration becomes to 0.75%, 0.85% and 0.1%, respectively. The solution is adjusted to a pH of 8.2 using a 1/10 N sodium hydroxide solution to thereby give a buffer solution for diluting the specimen.

EXAMPLE 4 hCG is dissolved in a concentration of 0.03% in a borate buffer solution. To 50 ml of the resulting solution is added an equal amount of a suspension of 10% polystyrene latex (average particle diameter of 0.54 microns) and heated at 37° C. for 30 minutes to thereby allow the polystyrene latex to absorb the hCG. After centrifugal separation, 500 ml of the stabilizer prepared in accordance with Example 2 is added to the precipitate. After settling at 4° C. for a night and centrifugal separation, the precipitate is again suspended in the buffer solution to thereby stabilize the hCG measuring reagent.

EXAMPLE 5

Human placental lactogen (hPL) is immunized to a rabbit to obtain an anti-hPL antiserum. The resulting anti-hPL antiserum is purified by salting out with sodium sulfate to thereby give an anti-hPL γ-globulin fraction. This fraction is then dissolved in a concentration of 0.06% in PBS. To 200 ml of this solution is added 200 ml of a 3.3% suspension of sheep red blood cells treated with formalin and tannic acid, mixed, heated at 37° C. for 10 minutes and then centrifugally separated to obtain the anti-hPL γ-globulin adsorbing blood cells. After blood cells are washed with PBS, 200 ml of the stabilizer prepared in the same way as in Example 2 are added, and settled for a night at 10° C. Thereafter, the anti-hPL γ-globulin adsorbing blood cells are centrifugally separated and again suspended in PBS.

EXAMPLE 6

Gonadotropin (hCG) is immunized to a rabbit to obtain an anti-hCG antiserum, and a γ-globulin fraction is purified from the resulting antiserum by salting out using sodium sulfate. The fraction is then dissolved in a concentration of 0.06% in GBS. To 20 ml of this solution is added 20 ml of a 10% suspension of styrene-divenylbenzene copolymer latex (average particle diameter of 0.3 microns) having introduced therein a hydroxyl group, and heated at 37° C. for 10 minutes to thereby allow the latex to adsorb the anti-hCG γ-globulin. After washing with GBS, 220 ml of the stabilizer prepared in Example 2 is added to the precipitate. After settling at 4° C. for a night, the latex is centrifugally separated and then suspended in GBS.

EXAMPLE 7 hPL is immunized to a rabbit to obtain an anti-hPL antiserum, and γ-globulin fraction is purified from the resulting antiserum by salting out with sodium sulfate. The fraction is dissolved in a concentration of 0.06% in PBS. To 20 ml of this solution is added an equal amount of a 10% suspension of styrene-divinylbenzene copolymer latex (average particle diameter of 0.3 microns), and then heated at 56° C. for 20 minutes thereby allow the solid particles to adsorb the γ-globulin fraction. The stabilizer prepared in accordance with Example 1 is added to the precipitate obtained by centrifugal separation and left standing at a low temperature for a night. The precipitate is collected by centrifugal separation and again suspended in PBS.

EXAMPLE 8

Estriol-16, 17-dihemisuccinate BSA is immunized to a rabbit to obtain an anti-estriol antiserum, and a γ-globulin fraction is purified from the resulting antiserum by the use of sodium sulfate. The fraction is dissolved in a concentration of 0.08% in GBS. To 5 ml of this solution is added a 10% suspension of styrene-divinylbenzene copolymer latex (average particle diameter of about 0.3 microns) and heated at 45° C. for one hour to thereby allow the latex to adsorb the anti-estriol γ-globulin. After centrifugal separation, a stabilizer prepared in accordance with Example 2 is added to the precipitate and allowed to settle at 4° C. for a night. After centrifugal separation of the latex, the precipitate is collected and again suspended in GBS.

What is claimed is:

1. A stabilizer for immunochemical measuring reagents consisting of a buffer solution containing cytochrome c and sodium azide.

2. A stabilizer as set forth in claim 1 wherein the content of the cytochrome c is 0.01–5%.

3. A stabilizer as set forth in claim 1 wherein the content of the sodium azide is 0.05–0.2%.

4. A stabilizer as set forth in claim 1 wherein the cytochrome c is either cytochrome c of horse heart muscle or yeast cytochrome c.

5. A stabilizer for immunochemical measuring reagents consisting of a buffer solution and a solution obtained by heating a solution containing cytochrome c and sodium azide at 100°–130° C. for 2–8 hours in an autoclave and removing the produced coagulated substance.

6. A stabilizer as set forth in claim 5 wherein the content of the cytochrome c is 0.01–5%.

7. A stabilizer as set forth in claim 5 wherein the content of the sodium azide is 0.05–0.2%.

8. A buffer solution containing one of the stabilizers as in one of claims 1–7.

9. A process for producing a stabilizer for an immunochemical reagent consisting essentially of the steps of dissolving cytochrome c in a solution containing sodium azide, heating the thus obtained solution at 100°–130° C. for 2–8 hours in an autoclave, removing the coagulated substance from the solution and bufferizing the thus obtained solution.

10. A process claimed in claim 9 wherein a buffering process comprises dialyzing the solution obtained in claim 9 for a night against a buffer solution.

11. A process claimed in claim 9 wherein the buffering process comprises adding to the solution obtained in claim 9 composite ingredients of a buffer solution.

12. A process for stabilizing an immunochemical measuring reagent consisting of carrier particles adsorbed with antigen or antibody, the stabilizing process comprising contacting cytochrome c and sodium azide with said carrier particles and allowing them to settle at 4°–10° C. for a night, centrifugally separating to obtain a precipitate, and suspending the precipitate in a buffer solution.

13. An immunochemical measuring reagent consisting of carrier particles adsorbed with antigen or antibody, the immunochemical measuring reagent being stabilized by the presence of a buffered solution containing cytochrome c and sodium azide.

14. A process for producing an immunochemical measuring reagent composed of carrier particles adsorbed with antigen or antibody, the process comprising contacting a solution containing 0.01–5.0% cytochrome c and 0.05–2% sodium azide with said carrier particles, settling them at 4°–10° C. for a night, centrifugally separating them to obtain precipitate, and suspending the precipitate in the buffer solution.

15. A method of maintaining, over an extended period of time, the sensitivity of measurement and specificity of a measuring reagent based on the immunochemical agglutination reaction or agglutination inhibition reaction which comprises adding to said measuring reagent a stabilizer consisting of a buffer solution containing 0.01–5% cytochrome c and 0.05–2% sodium azide.

* * * * *